United States Patent [19]

Bartek et al.

[11] Patent Number: 4,886,931

[45] Date of Patent: Dec. 12, 1989

[54] UPGRADING LOW MOLECULAR WEIGHT HYDROCARBONS

[75] Inventors: Joseph P. Bartek, Highland Hts.; James F. Brazdil, Jr., Mayfield Hts.; John M. Hupp, University Hts.; Robert K. Grasselli, Aurora, all of Ohio

[73] Assignee: The Standard Oil Company, Cleveland, Ohio

[21] Appl. No.: 58,016

[22] Filed: Jun. 4, 1987

[51] Int. Cl.$^4$ ............................................. C07C 2/00
[52] U.S. Cl. ................................... 585/500; 585/654; 585/656; 585/662; 585/700; 585/943
[58] Field of Search ............... 585/500, 415, 417, 418, 585/516, 654, 656, 658, 661, 662, 663, 700

[56] References Cited

U.S. PATENT DOCUMENTS

| | | | |
|---|---|---|---|
| 2,180,672 | 11/1939 | Frey | 196/10 |
| 4,172,810 | 10/1979 | Mitchell et al. | 252/465 |
| 4,205,194 | 5/1980 | Mitchell et al. | 585/407 |
| 4,239,658 | 12/1980 | Mitchell et al. | 252/465 |
| 4,334,116 | 6/1982 | Velenyi | 585/663 X |
| 4,443,644 | 4/1984 | Jones et al. | 585/500 |
| 4,443,647 | 4/1984 | Jones et al. | 585/500 |
| 4,443,649 | 4/1984 | Jones et al. | 585/500 |
| 4,450,310 | 5/1984 | Fox et al. | 585/400 |
| 4,544,786 | 10/1985 | Breder et al. | 585/500 |
| 4,547,608 | 10/1985 | Johnson | 585/500 |
| 4,620,057 | 10/1986 | Kimble | 585/500 |
| 4,658,076 | 4/1987 | Kolts | 585/500 |
| 4,658,077 | 4/1987 | Kolts | 585/500 |

FOREIGN PATENT DOCUMENTS

| | | |
|---|---|---|
| 8631168 | 3/1985 | Australia. |
| 946583 | 1/1964 | United Kingdom ............... 585/661 |

OTHER PUBLICATIONS

Keller, G. E. et al., Journal of Catalysis, 73, 9-19 (1982).
Otsuka et al., Chem. Letters, 1985, pp. 499-500.
Otsuka et al., Chem. Letters, 1986, pp. 903-906.
Lunsford et al, Symposium on the New Surface Science in Catalyses, etc., American Chemical Society Philadelphia Meeting, Aug. 26-31, 1984, pp. 920-926.
Matsuura et al, Chem. Letters, 1986, pp. 1981-1984.

*Primary Examiner*—William R. Dixon, Jr.
*Assistant Examiner*—James M. Hunter, Jr.
*Attorney, Agent, or Firm*—Raymond F. Keller; David J. Untener; Larry W. Evans

[57] ABSTRACT

A multi-component oxide catalyst comprising zinc and an alkali metal is described which is useful particularly for converting methane and/or natural gas to higher molecular weight hydrocarbon products such as ethane and ethylene. The catalyst is characterized by the formula $$Zn_a A_b M_c M'_d O_x$$

wherein
  A is Li, Na, K, or mixtures thereof;
  M is Al, Ga, Cr, La, Y, Sc, V, Nb, Ta, Cu or mixtures thereof;
  M' is Cs, Rb, Mg, Ca, Sr, Ba, Sm, Pb, Mn, Sb, P, Sn, Bi, Ti, Zr, Hf, or mixtures thereof;
  a is from about 1 to about 20;
  b is from about 0.1 to about 20;
  c is from about 0 to about 5;
  d is from about 0 to about 20; and
  x is a number needed to fulfill the valence requirements of the other elements; provided that
  (i) at least one of c and d is at least 0.1; and
  (ii) when M' is Sn, c must be at least 0.1. The process of the present invention involves contacting low molecular weight alkanes at elevated temperatures with oxygen and the catalyst of the invention for a period of time sufficient to provide the desired conversion.

19 Claims, No Drawings

UPGRADING LOW MOLECULAR WEIGHT HYDROCARBONS

FIELD OF THE INVENTION

This invention relates to the upgrading of low molecular weight hydrocarbons to form higher order hydrocarbons. More particularly, the present relates to novel multi-component oxide catalysts which are particularly effective in an oxidative process for the upgrading of low molecular weight alkanes. The catalysts are specially useful for upgrading methane and/or natural gas to ethane and ethylene.

BACKGROUND OF THE INVENTION

A major source of methane is natural gas which typically contains about 40–95% methane depending on the particular source. Other constituents include about 10% of ethane with the balance being made up of $CO_2$ and smaller amounts of propane, the butanes, the pentanes, nitrogen, etc.

Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Natural gas obtained from these sources is generally utilized as a fuel at the site.

Prior to commercial use, natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station. Processed natural gas typically comprises a major amount of methane, and minor amounts of ethane, propane, the butanes, the pentanes, carbon dioxide and nitrogen. Generally, processed natural gas comprises from about 70% to more than about 95% by volume of methane. Natural gas is used principally as a source of heat in residential, commercial and industrial service.

Most processed natural gas is distributed through extensive pipeline distribution networks. As natural gas reserves in close proximity to gas usage decrease, new sources that are more distant require additional transportation. Many of these distant sources are not, however, amenable to transport by pipeline. For example, sources that are located in areas requiring economically unfeasible pipeline networks or in areas requiring transport across large bodies of water are not amenable to transport by pipeline. This problem has been addressed in several ways. One such solution has been to build a production facility at the site of the natural gas deposit to manufacture one specific product. This approach is limited as the natural gas can be used only for one product, preempting other feasible uses. Another approach has been to liquefy the natural gas and transport the liquid natural gas in specially designed tanker ships. Natural gas can be reduced to 1/600th of the volume occupied in the gaseous state by such cryogenic processing, and with proper procedures, safely stored or transported. These processes, which involve liquefying natural gas to a temperature of about $-162°$ C., transporting the gas, and revaporizing it are complex and energy intensive.

Still another approach has been the conversion of natural gas to higher molecular weight hydrocarbons that can be easily handled and transported, preferably substantially liquid hydrocarbons. The conversion of natural gas to higher order hydrocarbons, especially ethane and ethylene, would retain the material's versatility for use as precursor materials in chemical processing. Known dehydrogenation and polymerization processes are available for the further conversion of ethane and ethylene to liquid hydrocarbons. In these ways, easily transportable commodities may be derived directly from natural gas at the wellhead. A drawback in implementing such processes has been in obtaining a sufficient conversion rate of natural gas to higher molecular weight hydrocarbons.

The conversion of methane to higher molecular weight hydrocarbons at high temperatures, in excess of about 1000° C. is known. These processes are, however, energy intensive and have not been developed to the point where high yields are obtained even with the use of catalysts. Some catalysts that are useful in these processes (e.g., chlorine) are corrosive under such operating conditions.

The catalytic oxidative coupling of methane at atmospheric pressure and temperatures of from about 500° C. to 1000° C. has been investigated by G. E. Keller and M. M. Bhasin. These researchers reported the synthesis of ethylene via oxidative coupling of methane over a wide variety of metal oxides supported on an alpha alumina structure in *Journal of Catalysis*, 73, 9–19 (1982). This article discloses the use of single component oxide catalysts that exhibited methane conversion to higher order hydrocarbons at rates no greater than 4%. The process by which Keller and Bhasin oxidized methane was cyclic, varying the feed composition between methane and nitrogen and air (oxygen) to obtain higher selectivities.

The conversion of methane to higher molecular weight hydrocarbons using metal oxide catalysts and oxides of carbon which are generated from the hydrocarbon is described in U.S. Pat. No. 2,180,672. The conversion generally is carried out at temperatures of from about 150°–350° C., and the oxides of carbon are consumed in the reaction.

Methods for converting methane to higher molecular weight hydrocarbons at temperatures in the range of about 500° C. to about 1000° C. are disclosed in U.S. Pat. Nos 4,443,644; 4,443,645; 4,443,646; 4,443,647; 4,443,648; and 4,443,649. The processes taught by these references provide relatively high selectivities to higher order hydrocarbons but at relatively low conversion rates, on the order of less than about 4% overall conversion. In addition to synthesizing hydrocarbons, the processes disclosed in these references also produce a reduced metal oxide which must be frequently regenerated by contact with oxygen. The preferred processes taught by these references entail physically separate zones for a methane contacting step and for an oxygen contacting step, with the reaction promoter recirculating between the two zones.

U.S. Pat. Nos 4,172,810; 4,205,194; and 4,239,658 disclose the production of hydrocarbons including ethylene, benzene, ethane, propane and the like, in the presence of a catalyst-reagent composition which comprises: (1) a Group VIII noble metal having an atomic number of 45 or greater, nickel, or a Group Ib noble metal having an atomic number of 47 or greater; (2) a Group VIb metal oxide which is capable of being reduced to a lower oxide; and (3) a Group IIa metal selected from the group consisting of magnesium and strontium composited with a passivated, spinel-coated refractory support or calcium composited with a passivated, non-zinc containing spinel-coated refractory support. The feed streams used in the processes disclosed in these patents do not contain oxygen. Oxygen is avoided for the purposes of avoiding the formation of coke in the catalyst. Oxygen is generated for the reaction from the catalyst; thus periodic regenerations of the catalysts are required.

U.S. Pat. No. 4,450,310 discloses a methane conversion process for the production of olefins and hydrogen comprising contacting methane in the absence of oxygen and in the absence of water at a reaction temperature of at least 500° C. with a catalyst comprising the mixed oxides of a first metal selected from lithium, sodium, potassium, rubidium, cesium and mixtures thereof, a second metal selected from beryllium, magnesium, calcium, strontium, barium, and mixtures thereof, and optionally a promoter metal selected from copper, rhenium, tungsten, zirconium, rhodium, and mixtures thereof.

West German Patent No. DE 32370792 to Baerns and Hinsen describes the use of supported single component oxide catalyst. The process utilizes low oxygen partial pressure to give a high selectivity for the formation of ethane and ethylene. The conversion of methane to such desired products, however, is low, on the order of from about 4 to about 7% conversion.

U.S. Pat. No. 4,658,076 and Australian published Patent Application No. 8654350A describe catalyst systems which consist essentially of either Group IA metals/zinc oxide; or Group IA metals/zinc oxide/-chloride ions, compounds containing chloride ions, tin, or compounds containing tin. The catalysts are reported as being useful in the oxidative conversion of feed organic compounds comprising methane to product organic compounds comprising higher hydrocarbons.

The oxidative coupling of methane to ethylene and ethane over lithium-promoted zinc oxide catalysts is described in an article by Matsuura et al, Chem. Letters, 1986, pp. 1981-84. Other alkali-promoted zinc oxides were also tested as catalysts for the oxidative coupling of methane, and of the alkali metals, lithium is reported to provide the best conversions and selectivity to ethane and ethylene.

The synthesis of ethylene with high selectivity and yield using a catalyst comprising the oxides of transition metals with lithium chloride has been reported by Otsuka et al, Chem. Letters, 1986, pp. 903-06. Of the transition metal oxides studied, manganese and nickel were reported to produce ethylene with the highest selectivity and yield.

European published Patent Application No. 198251 describes contact materials useful for the oxidative conversion of methane to higher hydrocarbons. The materials may be selected from the group consisting of (a) a component comprising at least one oxide of calcium, strontium or barium and, optionally, a component comprising chloride ions, compounds containing chloride ions, tin and compounds containing tin, or (b) a component comprising at least one metal from the group of sodium, potassium or compounds containing said metals, a component comprising at least one metal from Group IIA metals and compounds containing said metals, and, optionally, chloride ions, compounds containing chloride ions, tin or tin compounds, or (c) a component comprising a Group IA metal and compounds containing said metal, a component comprising calcium, strontium, barium or compounds containing said metals and, optionally, chloride ions, compounds containing chloride ions, tin or compounds containing tin.

U.S. Pat. No. 3,119,883 describes ZnO promoted with 1 to 10 mole percent Pb, Bi, Sn or Fe and up to 1 weight percent alkali metal as an oxydehydrogenation catalyst for ethane conversion to ethylene.

U.S. Pat. Nos 4,547,608 and 4,544,786 describe a method for converting methane to higher hydrocarbon products by contacting methane with a contact agent comprising (a) a reducible metal oxide such as lead oxide, (b) a support of at least two oxides such as the combination of an alkaline earth oxide with silica, alumina, or mixtures thereof, and (c) an alkali metal.

There continues to be a need for processes useful in converting light hydrocarbons such as methane and/or natural gas to higher molecular weight liquid hydrocarbons with high selectivity and conversion rates.

SUMMARY OF THE INVENTION

A multi-component oxide catalyst comprising zinc and an alkali metal is described which is useful particularly for converting methane and/or natural gas to higher molecular weight hydrocarbon products such as ethane and ethylene. The catalyst is characterized by the formula $$Zn_a A_b M_c M'_d O_x$$

wherein

A is Li, Na, K, or mixtures thereof;

M is Al, Ga, Cr, La, Y, Sc, V, Nb, Ta, Cu or mixtures thereof;

M' is Cs, Rb, Mg, Ca, Sr, Ba, Sm, Pb, Mn, Sb, P, Sn, Bi, Ti, Zr, Hf, or mixtures thereof;

a is from about 1 to about 20;

b is from about 0.1 to about 20;

c is from about 0 to about 5;

d is from about 0 to about 20; and x is a number needed to fulfill the valence requirements of the other elements; provided that (i) at least one of c and d is at least 0.1; and (ii) when M' is Sn, c must be at least 0.1.

The process of the present invention involves contacting low molecular weight hydrocarbons at elevated temperatures with oxygen and the catalyst of the invention for a period of time sufficient to provide the desired conversion.

DESCRIPTION OF THE PREFERRED EMBODIMENTS

As used herein, the phrases "low molecular weight hydrocarbons" or "lower molecular weight alkanes" refer to light hydrocarbon feedstocks which are typically methane, ethane, propane, butane and pentane, each of which is a major or minor constituent in natural gas. The above phrases also include natural gas. The phrase "higher order hydrocarbons" refers to the product of a reaction wherein a hydrocarbon is reacted to yield a hydrocarbon having at least one carbon atom more than contained in the reactant hydrocarbon.

The catalysts of the present invention which are useful in particular for converting low molecular weight hydrocarbons to higher molecular weight hydrocarbons or higher order hydrocarbons is characterized by the formula $$Zn_aA_bM_cM'_dO_x$$

wherein
A is Li, Na, K, or mixtures thereof;
M is Al, Ga, Cr, La, Y, Sc, V, Nb, Ta, Cu or mixtures thereof;
M' is Cs, Rb, Mg, Ca, Sr, Ba, Sm, Pb, Mn, Sb, P, Sn, Bi, Ti, Zr, Hf, or mixtures thereof;
a is from about 1 to about 20;
b is from about 0.1 to about 20;
c is from about 0 to about 5;
d is from about 0 to about 20; and
x is a number needed to fulfill the valence requirements of the other elements; provided that
  (i) at least one of c and d is at least 0.1; and
  (ii) when M' is Sn, c must be at least 0.1.

As can be noted from the formula, the catalysts must contain at least zinc and either lithium, sodium or potassium. These materials may be further modified by the addition of other elements including those identified as M and M'. Elements from each of the groups may be included singly or in combination. In one embodiment, the elements identified as M are present in the catalyst in amounts such that c is from about 0.1 to about 20, and more generally from about 0.1 to about 5. In another preferred embodiment, M is aluminum, galium, chromium or lanthinum. M' preferably is magnesium, chromium or cesium. Preferably, the value of a is from about 1 to about 15; the value of b is from about 0.1 to about 10 and d is from about 0.1 to about 10.

The catalysts can be prepared by any means known in the art. Impregnation of the hydroxide or hydroxy carbonate of zinc or a combination of these compounds of the various elements with alkali metal salts is particularly convenient. High surface area zinc oxide prepared from zinc fume such as KADOX ™ (of New Jersey Zinc) also may be used as a source of zinc. Some portion of the materials such as $ZrO_2$, $TiO_2$, $SnO_2$, MgO or $Al_2O_3$ may be present as preformed oxides or hydrous oxides before the remainder of the materials is added including the zinc and alkali metal compounds. The surface area of the catalyst and its final macroporous structure may be controlled in this manner. When supports are utilized, other inert materials such as alpha alumina, cordierite, calcium zirconate, silica, alumina-silica, silicon carbide, clay, etc., may be coated with the materials of this invention to also control the physical hardness and porosity.

The catalyst may be formed into bodies of sizes and shapes suitable for a variety of high productivity reactors. Small spherical particles may be made by spray drying a slurry of the components or by dropping such a slurry into a long column of oil. Catalyst powder may be agglomerated into spherical particles by pan granulation or coated onto inert particles by similar means. The active powders or precursor slurries may be coated on porous structures such as charcoal or polyurethane which are then burned away leaving a porous replica particle. The catalyst also may be coated on fibrous mats or on the inside of porous or non-porous reactor walls. Catalyst powders also may be formed into tablets, rings, hollowspheres, or extrudates by various known techniques.

In one embodiment, it is preferred that the catalyst be heat-treated prior to use in the conversion of low molecular weight hydrocarbons, although this is not required for the present invention. Heat treating has been found to increase the catalyst stability. The catalyst preferably is heat-treated to a temperature of from about 200° to about 700° C. or higher for a period of up to about 2 to 5 hours in a flowing oxygen/nitrogen stream. Such pretreatment may occur upon start-up of reactor used to convert the low molecular weight hydrocarbons to higher molecular weight hydrocarbons.

The following examples illustrate the preparation of some of the specific catalysts of this invention. Unless otherwise indicated in the following examples or elsewhere in the specification and claims, all parts and percentages are by weight and all temperatures are in degrees centigrade.

EXAMPLE 1

A catalyst characterized by the formula $$Li_2Zn_6Mg_5O_x$$

is prepared as follows. A solution of 93 parts of zinc nitrate hexahydrate in 150 parts of water and 2 parts of concentrated nitric acid is prepared and added to 25 parts of magnesium carbonate (41.2% MgO) in 100 parts of water. A solution of 4.3 parts of lithium hydroxide in 30 parts of water then is added to the resulting slurry. Further precipitation occurs when the pH is adjusted to 7.5–8 by the addition of 23 parts of ammonium carbonate and 85 parts of water. Most of the water evaporates with stirring, and the product is dried at 110° C. The product is heat-treated in air at 290° C. before grinding to size and storing.

EXAMPLE 2

The product characterized by the formula $$Li_2Al_{0.5}Zn_6Mg_5O_x$$

is prepared using the same proportions of zinc, magnesium and lithium compounds as used in the preparation of the catalyst of Example 1. An aluminum nitrate solution (9.6 parts in 20 parts water) is added to the zinc nitrate solution before it is added to the magnesium carbonate slurry. The lithium hydroxide solution is added, and the pH is adjusted. The slurry is dried and heat-treated as in Example 1.

EXAMPLE 3

The catalyst of this example is characterized by the formula $$Li_{0.5}Zn_6Zr_5O_x$$

A mixed zinc-zirconium hydroxy-carbonate powder is made by addition of a solution of 100 parts of ammonium carbonate in 580 parts of water to a solution of 91 parts of zinc nitrate hexahydrate and 75 parts zirconyl nitrate hydrate in 320 parts of water and 4 parts of nitric acid. The mixture is stirred (pH=7.2), filtered, and the residue is dried at 110° C. The powder is impregnated with lithium hydroxide (1.09 parts) dissolved in 31 parts of water, and the resulting damp solid is dried, first under vacuum with warming, and then at 110° C. in air.

A portion of the dried material is further heat-treated in flowing air at a temperature of 350° C. before use.

EXAMPLE 4

The catalyst of this example is represented by the formula $$Li_{0.5}Cs_{0.1}Zn_{11}O_x$$

A zinc hydroxy-carbonate powder is prepared by the addition of 72 parts of ammonium carbonate in 360 parts of water to a solution of 171 parts of zinc nitrate hexahydrate in 270 parts of water and 1 part of nitric acid. The mixture is stirred (pH=6.3) several hours and filtered. The residue is dried at 110° C. Two portions of the dried powder are impregnated with lithium hydroxide solution and the resulting damp solids are dried, first under vacuum with warming, and then at 110° C. in air. The dried powder is sized, and a portion of the zinc hydroxy-carbonate powder smaller than 35 mesh is impregnated with a mixed solution of lithium hydroxide and cesium nitrate. This mixture is partially agglomerated during rotary vacuum drying. When the agglomeration is sufficient, the rotation is stopped and the product granules dried further under vacuum and then at 110° C.

The catalyst of the present invention is particularly useful in the oxidative conversion of lower molecular weight hydrocarbons to higher molecular weight hydrocarbons. As mentioned earlier, the light hydrocarbon feedstocks are typically hydrocarbons containing from 1 to 5 carbon atoms such as methane, ethane, propane, butane, pentane, and mixtures thereof as well as natural gas. The natural gas can be either wellhead natural gas as described earlier, or process natural gas. The composition of processed natural gas varies with the needs of the ultimate user. A typical process natural gas composition contains from about 75–80% by volume of methane up to about 15% by volume of $CO_2$ and about 0.5 to 10% by volume of ethane, the balance being made up of propane, butane and nitrogen.

The process of the present invention utilizing the catalyst of the invention may be conducted in a variety of oxidation reactors including those with fixed or moving catalyst beds. Fluidized beds of the catalyst may be used which have relatively low feed velocities so that the catalyst is not substantially transported from the bed. On the other hand, faster fluid beds including transport line reactors may be used. The addition of oxygen may be concurrent with the methane feed or at other locations in the reactor. Supplemental oxygen may be added at further points or even via a porous wall.

When natural gas comprises a portion of the feedstream, the minor amounts of other lower molecular weight alkanes are upgraded in a manner similar to that of methane. Ethane may be converted to butane and propane. If the reaction contemplates recycling the unreacted natural gas, then the portion of the feedstream containing minor amounts of ethane, butane, propane and pentane may change, depending on the efficiency of the product recovery apparatus. These alkanes need not be fully removed from the reactor feedstreams. The resultant products are substantially higher order hydrocarbons.

The heat generated by the oxidative reaction when converting lower molecular weight hydrocarbons to higher molecular weight hydrocarbons may be conveyed from the catalyst in various ways, either through the walls of tubes containing the catalyst to a coolant contained in the reactor shell, or by contact with cooling coils immersed in the catalyst bed. Also, the reactor may be run in adiabatic mode, where the reacting gas carries away much of the heat, but the temperature of the catalyst becomes much greater than that of the incoming gas. This temperature rise may be sufficient to promote endothermic reactions such as dehydrogenations of paraffins to olefins or thermal cyclizations of olefins to aromatics in the downstream portions of the reactor.

The conversion of the lower molecular weight hydrocarbons to higher molecular weight hydrocarbons in accordance with the process of this invention may be conducted over a wide range of temperatures, oxygen:-hydrocarbon ratios, reaction pressures and contact times. Operating temperatures of from about 500 to about 1200° C., and more generally from about 600° to about 1000° C. can be utilized. The oxygen content of the feed can range from about 0.01 to about 1.5 times the hydrocarbon volume fraction, and gaseous diluents such as nitrogen, helium, argon, carbon dioxide or steam also may be present but are not required. The oxygen comprises up to about 50 volume percent of the reaction feedstream. The reactor pressures may range from about 0.5 to about 30 atm. Contact times between the feedstream and the catalyst may be varied as is evident to one skilled in the art depending upon other factors such as temperature and pressure. Generally, the lower molecular weight hydrocarbons will be in contact with the catalyst for a period of about 0.01 second to about 20 seconds although contact for a period of from about 0.1 second to about 2 seconds is sufficient in many applications.

The following specific examples (Runs) illustrate the process of the present invention for converting lower molecular weight hydrocarbons to higher molecular weight hydrocarbons. In these experiments, methane is oxidized over the catalyst by passing various methane/oxygen/nitrogen mixtures over 1.5 ml. of the catalyst in a heated quartz tube with an axial quartz thermowell passing through the bed. The reactor tube has an external diameter of 9 mm. and an internal diameter of 7 mm. The external diameter of the thermowell is about 3 mm. The bed is roughly 5 cm. long and is placed near the center of the heated zone of a 1-inch diameter by 12-inch long Lindberg laboratory furnace. The remainder of the heated portion of the reactor tube is filled with quartz chips to provide preheat and decrease the likelihood of side reactions downstream of the catalyst. The thermocouple at the center of the reactor reads 10 to 20 degrees higher than the furnace controller in the absence of reaction. The furnace control thermocouple is placed in a well through the side of the furnace such that only a short section is in the hot zone which accounts for this difference. The reaction temperature rises during operation because of the exothermicity of oxidation, and this peak temperature is determined by moving a thermocouple in the axial quartz well. The difference between the maximum temperature and the temperature in the absence of reaction, the "exotherm", varies with the activity of the catalyst and the amount of oxygen present.

Before each run, the catalyst is heat-treated in the reactor in a flowing oxygen/nitrogen steam. Water picked up during storage of the catalyst is removed by heating to 300° C. The catalysts then are heated to 700° C. gradually over a few hours and held at this temperature for 2 hours to complete the catalyst heat treatment. Reaction is started as soon as possible after the heat treatment, or if time does not permit, the catalyst is cooled to 300° C. where it is not expected to change or hydrate, and the catalyst is maintained at this temperature overnight or until the reaction is begun.

The feed rate is near 200 cc/min. total for all runs, and the catalyst volume is constant at 1.5 cc. so that contact time is nearly constant also. Weight space velocities (WWH) vary with the catalyst weight which varied with the bulk density of the catalyst. Surface area per unit weight also varies.

After the gas is passed through the reactor, ethane, ethylene, propylene, propane, butane, butenes and methane are separated on a 10-foot long gas chromatographic column with Poropak QS packing in a Hewlett-Packard Model 5711 Chromatograph equipped with a flame ionization detector. Relative molar responses according to Dietz are used to obtain the ratio of hydrocarbon products to methane from the flame detector peak area. These responses are close to the unit response per carbon atom rule for an equimolar mixture of $CH_4/C_2H_4/C_2H_6$ which applies to flame ionization of hydrocarbons which applies for this type of detector. Oxygen, nitrogen, methane, carbon dioxide and carbon monoxide are determined with Fisher 1200 gas chromatograph equipped with a thermal conductivity detector. In this chromatograph, the lighter gases are separated by a molecular sieve 13X column arranged in parallel with a column which separates $CO_2$ from the light gases and the $C_2$ and higher hydrocarbons. Methane conversion is determined by comparison of feed and product gas analyses from this chromatograph. Material balances are computed from all of the data.

Runs 1–15

In these runs, a methane-containing feed with a ratio of $CH_4/O_2/N_2$ of 1/0.21/2.5 is passed over zinc containing catalysts at different temperatures as indicated in the following Table I.

TABLE I

| Run | Catalyst | Furnace Temp °C. | Methane Conv. % Methane to Higher Hydrocarbons | Higher Order Hydrocarbon Selectivity (%) | $C_2H_4/C_2H_6$ |
|---|---|---|---|---|---|
| 1 | $Li_2Zn_6Mg_5O_x$ | 700 | 6.2 | 83.6 | 0.244 |
| 2 | " | 760 | 15.3 | 79.5 | 0.621 |
| 3 | " | 800 | 20.1 | 76.3 | 1.034 |
| 4 | " | 850 | 18.8 | 72.6 | 1.061 |
| 5 | $Li_{0.5}Cs_{0.1}Zn_{11}O_x$ | 700 | 10.3 | 79.2 | 0.372 |
| 6 | " | 760 | 16.0 | 69.1 | 0.734 |
| 7 | " | 760 | 21.8 | 77.02 | 0.992 |
| 8 | " | 800 | 15.1 | 64.11 | 0.786 |
| 9 | $Li_2Al_{0.5}Zn_6Mg_5O_x$ | 700 | 8.8 | 81.1 | 0.357 |
| 10 | " | 760 | 19.7 | 81.2 | 0.921 |
| 11 | " | 800 | 22.2 | 78.0 | 1.326 |
| 12 | $Li_{0.5}Zn_6Zr_5O_x$ | 700 | 5.4 | 37.3 | 0.387 |
| 13 | " | 760 | 7.9 | 48.5 | 0.506 |
| 14 | " | 800 | 9.1 | 52.9 | 0.636 |
| 15 | " | 850 | 9.2 | 49.5 | 0.942 |

As can be seen from the results summarized in Table I, $Li_2Zn_6MgO_x$ is the most selective catalyst under the conditions. The catalyst where the Li is partially compensated by trivalent Al, and the Zn is partially substituted by Mg results in the highest yields.

Conversion of ethane to ethylene is high for most of the catalysts once a temperature of 800° C. is reached. This conversion is shown by the ratio $C_2H_4/C_2H_6$. The catalyst promoted by both lithium and aluminum is particularly effective for this conversion at 800° C.

Runs 16–31

In these runs, the methane concentration is increased and the oxygen to methane ratio reduced. The $CH_4/O_2/N_2$ ratio is 1/0.11/0.26. As can be noted from the results shown in Table II, the selectivity toward higher hydrocarbons rises to the 80% range for many of the catalysts. Also, at the higher temperatures (near 800° C.) yields of higher hydrocarbons corresponding to 11 to 13% of the methane feed are achieved with some of the catalysts. In these runs, the conversion of ethane to ethylene in the product mix is limited by the relatively low oxygen concentration in the feed.

TABLE II

| Run | Catalyst | Furnace Temp° C. | Methane Conv. % Methane to Higher Hydrocarbons | Higher Order Hydrocarbon Selectivity (%) | $C_2H_4/C_2H_6$ |
|---|---|---|---|---|---|
| 16 | $Li_2Zn_6Mg_5O_x$ | 700 | 4.6 | 81.4 | 0.241 |
| 17 | " | 760 | 12.1 | 85.5 | 0.642 |
| 18 | " | 760 | 11.4 | 84.0 | 0.606 |
| 19 | " | 800 | 13.3 | 83.2 | 0.826 |
| 20 | " | 850 | 13.2 | 82.3 | 1.059 |
| 21 | $Li_{0.5}Cs_{0.1}Zn_{11}O_x$ | 700 | 3.2 | 63.8 | 0.181 |
| 22 | " | 760 | 9.2 | 72.4 | 0.524 |
| 23 | " | 800 | 10.5 | 73.9 | 0.688 |
| 24 | " | 850 | 10.9 | 75.4 | 0.939 |
| 25 | $Li_2Al_{0.5}Zn_6Mg_5O_x$ | 700 | 4.8 | 82.6 | 0.247 |
| 26 | " | 760 | 11.1 | 84.3 | 0.631 |
| 27 | " | 800 | 13.6 | 83.8 | 1.007 |
| 28 | $Li_{0.5}Zn_6Zr_5O_x$ | 700 | 6.1 | 55.7 | 0.374 |
| 29 | " | 760 | 7.3 | 59.4 | 0.457 |
| 39 | " | 800 | 7.9 | 61.3 | 0.605 |
| 31 | " | 850 | 7.8 | 60.7 | 1.038 |

Runs 32–49

In these runs, the oxygen concentration is twice that used in Runs 16–31, and the methane concentration is the same. The concentration ratio of $CH_4/O_2/N_2$ is 1/0.24/0.26. In these runs, as can be seen from the results summarized in Table III, methane conversion rises significantly, but selectivity is somewhat reduced. Conversion of ethane to ethylene becomes especially high at temperatures of about 900° C.

TABLE III

| Run | Catalyst | Furnace Temp °C. | Methane Conv. % Methane to Higher Hydrocarbons | Higher Order Hydrocarbon Selectivity (%) | $C_2H_4/C_2H_6$ |
|---|---|---|---|---|---|
| 32 | $Li_2Zn_6Mg_5O_x$ | 700 | 2.7 | 43.2 | 0.188 |
| 33 | " | 760 | 11.1 | 66.3 | 0.628 |
| 34 | " | 800 | 15.4 | 65.2 | 1.165 |
| 35 | " | 800 | 16.3 | 65.2 | 1.261 |
| 36 | " | 850 | 18.0 | 66.2 | 1.907 |
| 37 | " | 850 | 17.8 | 65.8 | 1.858 |
| 38 | $Li_{0.5}Cs_{0.1}Zn_{11}O_x$ | 700 | 1.1 | 33.0 | 0.133 |
| 39 | " | 760 | 8.4 | 58.7 | 0.603 |
| 40 | " | 800 | 15.3 | 61.8 | 1.218 |
| 41 | " | 800 | 15.7 | 62.6 | 1.261 |
| 42 | $Li_2Al_{0.5}Zn_6MgO_x$ | 700 | 0.2 | 22.1 | 0.086 |
| 43 | " | 760 | 1.8 | 42.7 | 0.235 |
| 44 | " | 800 | 5.1 | 63.1 | 0.472 |
| 45 | " | 850 | 14.0 | 66.8 | 1.450 |

TABLE III-continued

| Run | Catalyst | Furnace Temp °C. | Methane Conv. % Methane to Higher Hydrocarbons | Higher Order Hydrocarbon Selectivity (%) | $C_2H_4/C_2H_6$ |
|---|---|---|---|---|---|
| 46 | " | 850 | 13.0 | 61.5 | 1.437 |
| 47 | " | 900 | 15.5 | 61.0 | 2.604 |
| 48 | $Li_{0.5}Zn_6Zr_5O_x$ | 700 | 11.0 | 51.2 | 0.725 |
| 49 | " | 700 | 11.4 | 52.5 | 0.759 |

As can be seen from the above runs, the catalysts of the present invention which contain zinc oxide as a principle component are useful catalysts for methane oxidative coupling, particularly at higher temperatures where the yields of ethylene are higher. It should be apparent to those skilled in the art that while the invention has been explained in relation to its preferred embodiments, it is to be understood that various modifications in the invention can be made upon reading the specification. For example, the selection of precursor catalyst component compounds, catalyst formulations, methane/oxygen ratios, and the various reaction conditions can be varied without departing from the spirit of the invention. Therefore, it is to be understood that the invention disclosed herein is intended to include such modifications and variations as well as equivalent embodiments which are within the scope of the appended claims.

We claim:

1. A process for the conversion of low molecular weight alkanes to higher molecular weight hydrocarbons comprising contacting said low molecular weight alkanes, at an elevated temperature, with oxygen and a catalyst of the formula $$Zn_aA_bM_cM'_dO_x$$

wherein

A is Li, Na, K, or mixtures thereof;

M is Al, Ga, Cr, La, Y, Sc, V, Nb, Ta, Cu or mixtures thereof;

M' is Cs, Rb, Mg, Ca, Sr, Ba, Sm, Pb, Mn, Sb, P, Sn, Bi, Ti, Zr, Hf, or mixtures thereof;

a is from about 1 to about 20;

b is from about 0.1 to about 20;

c is from about 0 to about 5;

d is from about 0 to about 20; and x is a number needed to fulfill the valence requirements of the other elements; provided that (i) at least one of c and d is at least 0.1; and (ii) when M' is Sn, c must be at least 0.1.

2. The process of claim 1 wherein said low molecular weight alkanes comprise predominantly methane.

3. The process of claim 1 wherein said higher molecular weight hydrocarbons are predominantly ethane and ethylene.

4. The process of claim 1 wherein the elevated temperature is from about 500° C. to about 1200° C.

5. The process of claim 1 wherein said oxygen comprises up to about 50 volume percent of the reaction feedstream.

6. The process of claim 1 wherein a diluent gas is present.

7. The process of claim 1 wherein the elevated temperature is from about 600° C. to about 1000° C.

8. The process of claim 1 wherein the low molecular weight alkanes are in contact with said catalyst for a period of about 0.01 second to about 20 seconds.

9. The process of claim 1 wherein the low molecular weight alkanes are in contact with said catalyst for a period of from about 0.1 second to about 2 seconds.

10. The process of claim 1 wherein c is from about 0.1 to about 5.

11. The process of claim 1 wherein M is Al, Ga, Cr, or La.

12. The process of claim 1 wherein d is at least 0.1 and c is 0.

13. The process of claim 1 wherein a is from about 1 to about 10.

14. The process of claim 1 wherein b is from about 0.1 to about 10.

15. The process of claim 1 wherein A is Li.

16. The process of claim 1 wherein M is Al.

17. The process of claim 1 wherein M' is Mg, Zr, or Cs.

18. The process of claim 1 wherein said catalyst is supported on an inert carrier.

19. The process of claim 18 wherein said inert carrier is selected from alumina, silica, zirconia, alumina-silica, silicon carbide and clay.

* * * * *